United States Patent [19]

Marion

[11] 4,110,359
[45] Aug. 29, 1978

[54] PRODUCTION OF CLEANED AND PURIFIED SYNTHESIS GAS AND CARBON MONOXIDE

[75] Inventor: Charles P. Marion, Mamaroneck, N.Y.

[73] Assignee: Texaco Development Corporation, New York, N.Y.

[21] Appl. No.: 749,657

[22] Filed: Dec. 10, 1976

[51] Int. Cl.$^2$ .................. C07C 27/06; C07C 29/16; C07C 51/10; C01B 2/16
[52] U.S. Cl. .................. 260/449.5; 252/373; 260/532; 260/541; 423/415 A; 423/246; 423/248
[58] Field of Search .................. 260/449.5, 532, 541; 252/373; 423/415 A, 246, 248

[56] References Cited

U.S. PATENT DOCUMENTS

| | | | |
|---|---|---|---|
| 2,650,246 | 8/1953 | Boaden et al. | 260/532 |
| 2,980,521 | 4/1961 | Dille et al. | 260/373 X |
| 3,116,978 | 1/1964 | Marullo et al. | 260/532 X |
| 3,689,533 | 6/1972 | Schultz | 260/532 X |
| 3,772,380 | 11/1973 | Paulik et al. | 260/532 X |
| 3,920,717 | 11/1975 | Marion | 26/449.5 |
| 3,923,880 | 12/1975 | Westlake et al. | 260/532 |

*Primary Examiner*—Howard T. Mars
*Attorney, Agent, or Firm*—Thomas H. Whaley; Carl G. Ries; Albert Brent

[57] ABSTRACT

A continuous process for simultaneously producing a stream of cleaned purified synthesis gas having a mole ratio $H_2/CO$ in the range of about 2 to 12, and a separate stream of CO-rich gas. In one embodiment of the process, cleaned and purified methanol synthesis gas and substantially pur carbon monoxide are produced. Methanol may be synthesized and optionally catalytically reacted with the substantially pure carbon monoxide to produce acetic acid. In the subject process, the effluent gas stream directly from a free-flow unpacked noncatalytic partial-oxidation synthesis gas generator is split into two streams which are simultaneously processed in two separate trains. In the first train, one of the split streams is cooled by indirect heat exchange in a gas cooler and then further processed to produce a stream of cleaned and purified synthesis gas, a $H_2$-rich gas stream, and the product stream of CO-rich gas and preferably substantially pure CO. Simultaneously, the second split stream in the second train is cooled by direct quenching in water in a quench drum, cleaned, subjected to catalytic water-gas-shift reaction, and purified to produce a second $H_2$-rich gas stream. The product stream of cleaned and purified synthesis gas having a mole ratio $H_2/CO$ in the range of about 2 to 12 is then produced by mixing together at least a portion of the cleaned and purified synthesis gas stream from the first train with 0 to 100 volume % of the $H_2$-rich gas stream from the first train and at least a portion of the $H_2$-rich gas stream from the second train.

28 Claims, 2 Drawing Figures

PRODUCTION OF CLEANED AND PURIFIED SYNTHESIS GAS AND CARBON MONOXIDE

BACKGROUND OF THE INVENTION

1. Field of the Invention

This is a partial oxidation process in which synthesis gas having a controlled $H_2/CO$ mole ratio and a CO-rich gas or substantially pure CO are simultaneously produced. Methanol may be made from the synthesis gas and reacted with the CO-rich gas or substantially pure CO to produce acetic acid.

2. Description of the Prior Art

Synthesis gas may be prepared by the partial oxidation of a fossil fuel with a free-oxygen-containing gas, optionally in the presence of a temperature moderator. The effluent gas stream from the gas generator is cooled below the equilibrium temperature for the desired gas composition by, for example, direct immersion in water in the quench drum such as described in coassigned U.S. Pat. No. 2,896,927. By this method of gas cooling the sensible heat in the effluent gas stream is used to produce steam in the product gas.

Alternatively, the effluent gas stream from the gas generator may be cooled in a syngas cooler, such as shown in coassigned U.S. Pat. No. 3,920,717. However, by this method of gas cooling the effluent gas stream does not become saturated with the water required for subsequent water-gas shift reaction. Further excess solid particles entrained in the gas stream may become troublesome. In coassigned U.S. Pat. No. 3,929,429 in order to prepare an oil-carbon dispersion and a separate water-carbon dispersion which are simultaneously fed to a gas generator for producing fuel gas, a portion of the effluent gas stream is cooled in a waste heat boiler and then scrubbed with oil and another stream is quenched in water. Noncatalytic thermal shift is used to adjust the $H_2/CO$ mole ratio of a single stream of synthesis gas in coassigned U.S. Pat. No. 3,920,717.

SUMMARY

In the subject process, the effluent gas stream directly from a free-flow unpacked noncatalytic partial-oxidation synthesis gas generator, having an $H_2/CO$ mole ratio in the range of about to 0.5 to 1.9, is split into two gas streams. One gas stream is then processed in a first train comprising the following steps: cooling in a gas cooler by indirect heat exchange with boiler-feed water, scrubbing with water to remove any solid particles, cooling below the dew point to separate water, and removing gaseous impurities in a first gas-purification zone to produce a stream of cleaned and purified synthesis gas having a $H_2/CO$ mole ratio in the range of about 0.5 to 1.5. A portion of this stream of synthesis gas is introduced into a separation zone and separated into a stream of CO-rich product gas, preferably substantially pure CO, and a $H_2$-rich gas stream. Simultaneously, the other split gas stream from the gas generator is processed in a second train comprising the following steps: quenching ad scrubbing with water to remove the solid particles produced, catalytic water-gas shifting, cooling and condensing out water, and removing gaseous impurities in a second purification zone to produce a stream of clean hydrogen-rich gas.

At least a portion of the remaining portion of the cleaned and purified stream of synthesis gas from the first train is mixed with from about 0 to 100 volume % of the $H_2$-rich gas stream from the first train and at least a portion of the $H_2$-rich gas stream from the second train to produce the clean and purified synthesis gas product stream having an $H_2/CO$ mole ratio in the range of about 2 to 12.

In another embodiment, methanol synthesis gas having a mole ratio $H_2/CO$ in the range of about 2 to 4 is produced by the aforesaid process and catalytically converted into a stream of raw methanol. Pure methanol is obtained by purifying this stream. Optionally at least a portion of the pure methanol may be catalytically reacted with at least a portion of said product stream of substantially pure carbon monoxide to produce a stream of crude acetic acid which may be purified to produce glacial acid.

BRIEF DESCRIPTION OF THE DRAWING

The invention will be further understood by reference to the accompanying drawing.

DESCRIPTION OF THE INVENTION

In the first step of the subject process, raw synthesis gas, substantially comprising hydrogen and carbon monoxide and having a mole ratio ($H_2/CO$) in the range of about 0.5 to 1.9, is produced by partial oxidation of a hydrocarbonaceous fuel with substantially pure oxygen in the presence of steam in the reaction zone of an unpacked free-flow noncatalytic partial-oxidation gas generator. The steam-to-fuel weight ratio in the reaction zone is in the range of about 0.1 to 5, and preferably about 0.2 to 0.7. The atomic ratio of free oxygen to carbon in the fuel (O/C ratio), is in the range of about 0.6 to 1.6, and preferably about 0.8 to 1.4. The reaction time is in the range of about 1 to 10 seconds, and preferably about 2 to 6 seconds.

The raw synthesis gas stream exits from the reaction zone at a temperature in the range of about 1300° to 3000° F., and preferably 2000° to 2800° F., and at a pressure in the range of about 1 to 250 atmospheres, and preferably 15 to 150 atmospheres.

The composition of the raw synthesis gas leaving the gas generator is about as follows, in mole percent: $H_2$ 60 to 29, CO 31 to 57, $CO_2$ nil to 5, $H_2O$ nil to 20, $CH_4$ nil to 25, $H_2S$ nil to 2, COS nil to 0.1, $NH_3$ to 5, $N_2$ nil to 1, and A nil to 0.5. There may also be present particulate carbon in the range of nil to 20 weight % (basis carbon content in the original feed), and ash in the amount of nil to 60 weight % of the original hydrocarbonaceous feed.

The synthesis gas generator comprises a vertical cylindrically shaped steel pressure vessel lined with refractory, such as shown in coassigned U.S. Pat. No. 2,809,104. A typical quench drum is also shown in said patent. A burner, such as shown in coassigned U.S. Pat.

No. 2,928,460, may be used to introduce the feed streams into the reaction zone.

A wide range of combustible carbon-containing organic materials may be reacted in the gas generator with a free-oxygen containing gas, optionally in the presence of a temperature-moderating gas, to produce the synthesis gas.

The term hydrocarbonaceous as used herein to describe various suitable feedstocks is intended to include gaseous, liquid, and said hydrocarbons, carbonaceous materials, and mixtures thereof. In fact, substantially any combustible carbon-containing organic material, or slurries thereof, may be included within the definition of the term "hydrocarbonaceous." For example, there are (1) pumpable slurries of solid carbonaceous fuels, such as coal, particulte carbon, petroleum coke, concentrated sewer sludge, and mixtures thereof, in a vaporizable liquid carrier, such as water, liquid hydrocarbon fuel, and mixtures thereof; (2) gas-solid suspensions such as finely ground solid carbonaceous fuels dispersed in either a temperature-moderating gas or in a gaseous hydrocarbon; and (3) gas-liquid-solid dispersions, such as atomized liquid hydrocarbon fuel or water and articulate carbon dispersed in a temperature moderating gas. The hydrocarbonaceous fuel may have a sulfur content in the range of about 0 to 10 wt. percent and an ash content in the range of about 0 to 60 wt. percent.

The term liquid hydrocarbon, as used herein to described suitable liquid feedstocks, is intended to include various materials, such as liquefied petroleum gas, petroleum distillates and residua, gasoline, naphtha, kerosine crude petroleum, asphalt, gas oil, residual oil, tar-sand oil and shale oil, coal derived oil, aromatic hydrocarbons (such as benzene, toluene, xylene fractions), coal tar, cycle gas oil from fluid-catalytic-cracking operations, furfural extract of coker gas oil, and mixtures thereof.

Gaseous hydrocarbon fuels, as used herein to describe suitable gaseous feedstocks, include methane, ethane, propane, butane, pentane, natural gas, water-gas, coke-oven gas, refinery gas, acetylene tail gas, ethylene off-gas, synthesis gas, and mixtures thereof. Solids, gaseous, and liquid feeds may be mixed and used simultaneously; and these may include paraffinic, olefinic, acetylenic, naphthenic, and aromatic compounds in any proportion.

Also included within the definition of the term hydrocarbonaceus are oxygenated hydrocarbonaceous organic materials including carbohydrates, cellulosic materials, aldehydes, organic acids, alcohols, ketones, oxygenated fuel oil, waste liquids and by-products from chemical processes containing oxygenated hydrocarbonaceous organic materials and mixtures thereof.

The hydrocarbonaceous feed may be at room temperature, or it may be preheated to a temperature up to as high as about 600° to 1200° F. but preferably below its cracking temperature. The hydrocarbonaceous feed may be introduced into the gas-generator burner in liquid phase or in a vaporized mixture with the temperature moderator.

The need for a temperature moderator to control the temperature in the reaction zone depends in general on the carbon-to-hydrogen ration of the feedstock and the oxygen content of the oxidant stream. A temperature moderator may not be required with some gaseous hydrocarbon fuels; however, generally one is used with liquid hydrocarbon fuels and with substantially pure oxygen. Steam may be introduced as a temperature moderator in admixture with either or both reactant streams. Alternatively, the temperature moderator may be introduced into the reaction zone of the gas generator by way of a separate conduit in the burner.

The term free-oxygen-containing gas as used herein means substantially pure oxygen, i.e. greater than about 95 mole % oxygen (the remainder usually comprising $N_2$ and rare gases). Free-oxygen-containing gas may be introduced by way of the partial-oxidation burner at a temperature in the range of about ambient to 1800° F.

The raw synthesis gas exiting from the reaction zone of the gas generator is immediately split into two streams which are then simultaneously processed in two separate trains. In the first train no water-gas shiftng takes place, whereas in the second train water-gas shifting of the crude gas stream does take place.

The split of the raw synthesis gas between the two trains may be calculated by material and heat balances. The calculated split may be then adjusted, if necessary, after actual operation. Accordingly, said calculations take into consideration the compositions of the hydrocarbonaceous fuel and the raw synthesis gas, the amount and desired composition of the clean purified synthesis gas produce stream, the desired amount of substantially pure carbon monoxide product gas, the desired amount and efficiency of the catalytic water-gas shift conversion, the efficiency of the CO-separation zone, and the desired amount of by-product stream. For example, from about 20 to 80 volume % and preferably about 30 to 50 volume % of the raw synthesis gas leaving the reaction zone of the gas generator may be directly introduced into a quench drum containing water, in the second train. The remainder of the raw synthesis gas from the gas generator may be passed through an insulated transfer line, and directly into a syngas cooler, in the first train, in which the hot gases are passed in indirect heat exchange with boiling water, thereby cooling the gas stream to a temperature in the range of about 350° to 750° while simultaneously producing by-product steam.

The by-product steam may be used elsewhere in the process where required. Further, it may be produced at a pressure which is greater than that in the gas generator. Portions of the by-product steam may be used, for example, as the temperature moderator in the gas generator, as a carrier for the hydrocarbonaceous fuel, or as the working fluid in an expansion turbine; i.e., turbocompressor or turboelectric generator. The steam may also be used to power an air-separation unit that produces the substantially pure oxygen used in the gas generator.

The amount of solid particles i.e., selected from the group: particulate carbon, ash, and mixtures thereof, entrained in the raw synthesis gas leaving the reaction zone is dependent on the type of hydrocarbonaceous fuel and the atomic ratio (O/C) in the reaction zone. A small amount of entrained particulate carbon i.e., about 1-2 wt. % (basis weight of C in the hydrocarbonaceous feed), is recommended to increase the life of the refractory lining the gas generator.

The quench drum is located below the reaction zone of the gas generator, and the split stream of raw synthesis gas which it receives carries with it substantially all of the slag and a substantial part of the particulate-carbon soot leaving the reaction zone of the gas generator. However, to prevent plugging downstream catalyst beds and contaminating liquid-solvent absorbents used in subsequent gas-purification steps, the process gas streams in both trains may be further cleaned by contact with scrubbing fluids in separate cleaning zones one located in each train. By this means the amount of solid particles in the process gas steams may be reduced to less than about 3 parts per million (ppm) an preferably to less than about 1 ppm.

Any suitable means may be used for cleaning entrained solid particles from the process gas streams. For example the gas stream leaving the gas cooler in the first train may be contacted with a scrubbing fluid, such as water or liquid hydrocarbon in one or more steps in a gas-scrubbing zone, such as shown in coassigned U.S. Pat. No. 3,544,291. On the other hand, the process gas stream leaving the quench drum in the second train is preferably contacted with water only, in a separate scrubbing zone. By this means, the mole ratio $H_2O/CO$ in the process gas steam in the second train may be increased to a value in the range of about 2 to 5, and preferably 2.5 to 3.5 by vaporizing water during the quenching and scrubbing steps. This ratio is suitable for the next step in the second train, in which the water-gas shift reaction takes place and $H_2O$ and $CO$ in the process gas stream react to produce $H_2$ and $CO_2$. The water-gas shift step will be described later.

The solids dispersed in scrubbing fluid from the separation zones, may be returned to the gas generator as at least a portion of the feed. Thus, if the gas stream is scrubbed with water, the dispersion of particulate carbon and water which is formed may be concentrated or separated by conventional means to yield clarified water. This water may be recycled to an orifice, nozzle, or venturi scrubber in the gas cleaning zone. Carbon concentration may be effected by any suitable means; e.g., filtration, centrifuge, gravity settling, or by well-known liquid hydrocarbon extraction, such as the process described in coassigned U.S. Pat. No. 2,992,906.

The gas stream leaving the cleaning zone in the first train is optionally cooled below the dew point and then introduced into a knockout or separation vessel in which substantially all of the water is removed. Then at least a portion, but preferably all of the gas stream is introduced into a conventional gas purification zone in which any remaining $H_2O$ and at least one gaseous impurity from the group $CO_2$, $H_2S$, $COS$, $NH_3$, and $CH_4$ is removed. Optionally, a portion of the gas stream may by-pass the gas purification zone. The stream of by-pass gas may be then combined downstream with the purified gas stream.

Any suitable conventional process may be used for purifying the gas stream. Typical gas purification processes may involve refrigeration and physical or chemical absorption with a solvent, such as methanol, N-methyl-pyrrolidone, triethanolamine, propylene carbonate, or alternatively with hot potassium carbonate.

Advantageously, when methanol is used as the solvent, a portion of the product methanol may be used as make-up to the gas-purification zone. By scrubbing the synthesis gas with methanol at 0° C and 10 atmospheres, 100 volumes of $CO_2$ are absorbed per volume of methanol. This concentration is increased to 270 vol/vol at −30° C. At a high partial pressure of $CO_2$ e.g. 250 psi. methanol offers a very high absorption power. Similarly, cold methanol is an excellent selective solvent for separating $H_2S$ and $COS$ from $CO_2$. For example, the gas stream may be washed with cold methanol and the total sulfur, $H_2S + COS$, may be reduced to less than 0.1 ppm. By selective absorption of $H_2S$ and $COS$ a concentration of high sulfur in the off-gas is obtained, that contributes toward economic sulfur recovery.

In physical absorption processes, most of the $CO_2$ absorbed in the solvent may be released by simple flashing. The rest may be removed by stripping. This may be done most economically with nitrogen. Nitrogen may be available as a low cost by-product when a conventional air separation unit is used for producing substantially pure oxygen (95 mole % $O_2$ or more) for use as the free-oxygen containing gas in the synthesis gas generator. The regenerated solvent is then recycled to the absorption column for reuse. When necessary, final cleanup may be accomplished by passing the gas stream through iron oxide, zinc oxide, or activated carbon to remove residual traces of $H_2S$ or organic sulfur. Similarly, the $H_2S$ and $COS$-containing solvent may be regenerated by flashing or by stripping with nitrogen or, alternatively, by heating and refluxing at reduced pressure without using an inert gas. The $H_2S$ and $COS$ may be then converted into sulfur by a suitable process. For example, the Claus process may be used for producing elemental sulfur from $H_2S$, as described in Kirk-Othmer Encyclopedia of Chemical Technology, Second Edition Volume 19, John Wiley, 1969, Page 352. Excess $SO_2$ may be removed and discarded in chemical combination with limestone, or by means of a suitable commercial extraction process.

In an alternate gas purification scheme, from about 30 to 95% of the carbon dioxide may be removed from the synthesis gas stream, along with substantially all of the $H_2S$, by an autorefrigeration process. For example, references is made to coassigned U.S. Pat. No. 3,614,872 in which a stream of shifted synthesis gas is separated into an enriched hydrogen stream and an enriched carbon-dioxide stream by counter-current cooling with a departing stream of liquid $CO_2$ whch is expanded and vaporized to produce low temperature.

The cleaned and purified synthesis gas stream leaves the gas purification zone in the first train at a temperature in the rante of about −80° to 250° F. and at a pressure in the range of about 10 to 450 atmospheres (preferably substantially equal to the pressure in the reaction zone of the synthesis gas generator, less ordinary line drop). The composition of this cleaned and purified stream of synthesis gas follows: $H_2$ 70 to 30, CO 30 to 60, $CO_2$ nil to 20, $H_2O$ nil to 5, $NH_3$ nil to trace, $CH_4$ nil to 2, A nil to 2, $N_2$ nil to 15, $H_2S$ nil, and COS nil.

The aforesaid stream of cleaned and purified synthesis gas is split into two streams, depending upon the amount and composition of the carbon monoxide-rich gas required and the desired composition of the product stream of cleaned and purified synthesis gas. The split may be predetermined by material balances. Thus from about 5 to 50 volume % of the stream of cleaned and purified synthesis gas leaving the gas purification zone in the first train may be introduced into a carbon monoxide-separation zone, in which the following two gas streams are produced; (1) a CO-rich gas stream (preferably substantially pure carbon monoxide, comprising 95–99 mole % CO) and (2) a stream of $H_2$-rich gas. The $H_2/CO$ mole ratio of the remainder of the stream of cleaned and purified synthesis gas is then increased by mixing at least a portion and preferably all of it with at least one stream of $H_2$-rich gas to produce a stream of synthesis gas having a mole ratio, $H_2/CO$, in the range of about 2 to 12, in a manner to be described further. Optionally, from about 0 to 50 volume % of the aforesaid remainder of the stream of cleaned and purified synthesis gas may be removed from the system and used as a by-product.

Any suitable conventional process may be used for separating the carbon monoxide from the rest of said intermediate stream of cleaned and purified synthesis gas. Cryogenic cooling or physical absorption with a liquid solvent e.g. copper ammonium acetate or cuprous aluminum chloride solutions may be employed.

One system for removing CO from the gas stream by physical absorption in cold copper liquor in a CO-absorption column will be described below. Upon applying heat and releasing the pressure on the copper liquor in a copper-liquor regeneration column, a relatively pure carbon monoxide is obtained. The reaction is shown in Equation I. $Cu_2(NH_3)^{++}_4 + 2CO + 2NH_3^{++} \rightarrow Cu_2(NH_4)_6(CO)_2^{++}$ (I)

Thus, the effluent gas stream from the acid-gas scrubber may be contacted in a conventional packed or tray-type column with a countercurrent flowing stream of, for example, curpous acetate dissolved in aqua-ammonia solution. The temperature is preferably in the range of about 32° to 100° F. and the pressure is preferably in the range of about 50 to 600 atm. Preferably, the pressure in the CO separation zone is substantially the same as that in the gas generator, less ordinary pressure drop in the lines and equipment. By keeping the pressure in the gas generator high enough, a gas compressor may be avoided between the acid-gas-absorption column and the CO-absorption column.

A typical analysis (by weight %) of the copper-liquor solution may include the following: $Cu^+$ 10; $Cu^{++}$ 2.2; $CO_3^=$ (carbonate) 13.9; $HCO_3^-$ (bicarbonate) 1.3; and $NH_4^+$ 16.5. The acid radical in the aqueous solution may be either carbonate, formate, or acetate.

Regeneration of the copper liquor and release of the CO-rich gas stream takes place in a copper-liquor regenerator. The pressure difference between the scrubber and the regenerator is about 68 to 204 atm. e.g. 109 atm. By the reduction of pressure and the addition of heat and a free-oxygen containing gas, e.g. air, pure $O_2$, and mixtures thereof, the direction of Equation I may be reversed and the carbonate and bicarbonate ions may be regenerated. The normal temperature range in the regenerator may be about 170° to 180° F. Fresh make-up ammonia and, for example, acetic acid may be added to the copper liquor in the regenerator in order to maintain the proper solution chemistry. Optionally, the acetic acid may be produced subsequently in one embodiment of the subject process.

The CO-rich gas stream produced in the first train may have the following composition in mole % : CO 60 to 99; $N_2$ nil to 20; $CO_2$ 2 to 15; $H_2$ 2 to 8; $CH_4$ nil to 1; $NH_3$ nil to 5; and A nil to 1. Preferably by further purification, substantially pure carbon monoxide (95–99 mole % CO) may be produced.

The $H_2$-rich gas stream produced in the first train may ocmprise in mole % : $H_2$ 98 to 60; CO nil to 5; $CO_2$ nil to 5; $CH_4$ nil to 5; A nil to 4; $N_2$ nil to 20, and $NH_3$ nil to trace.

In the second train including the catalytic water-gas shift reaction, the soot-free gas stream is preferably introduced into a conventional catalytic water-gas shift reaction zone at an inlet temperature in the range of about 350° to 700° F. CO and $H_2O$ are reacted over a conventional water-gas-shift catalyst to produce additional $H_2$ and $CO_2$. A suitable water-gas-shift catalyst may comprise iron oxide mixed with Cr oxide and promoted by 1 to 15 wt.% of an oxide of another metal, such as K, Th, U, Be, or Sb. Reaction occurs at about 500° to 1050° F. Alternatively, cobalt molybdate on alumina may be used as the water-gas shift catalyst at a reaction temperature in the range of about 500° to 900° F. Co-Mo catalysts comprise, in weight percent: CoO 2–5, $MoO_3$ 8–16, MgO nil-20, and $Al_2O_3$ 59–85. Another low-temperature shift catalyst comprises a mixture of copper and zinc salts or oxides in a weight ratio of about 3 parts by weight zinc to 1 part copper.

Next, substantially all of the $H_2O$ is removed from the gas stream in the second train. For example, the clean gas stream may be cooled to a temperature below the dew point of water by conventional means to condense out and to separate $H_2O$. Optionally, the gas stream may be substantially dehydrated by contact with a desiccant, such as alumina.

At least a portion, and preferably all of the clean dry gas stream in the second train is subjected to further purification in a second gas purification zone. Optionally, a portion of the clean dry second-train gas stream may by-pass the second gas purification zone. The stream of by-pass gas may be then combined downstream with the purified gas stream. The second gas purification zone may comprise any suitable conventional system. For example, the second gas purification zone may be similar to the one described previously in connection with the purification of the gas stream in the first train. The second gas purification zone may employ physical absorption with a liquid solvent, for example, cold methanol, N-methylpyrrolidone, and dimethyl ether of polyethylene glycol. Optionally, purification of the dry gas stream may include cooling to a temperature in the range of about $-70°$ to $-50°$ F. to condense out and to separate a liquid stream comprising from about 0 to 70 volume % of the $CO_2$, $H_2S$, and COS originally present, depending upon the pressure and the amount present in the raw gas. The composition of the stream of hydrogen-rich gas leaving the purification zone of the second train follows:

$H_2$ 98 to 60; CO nil to 5; $CO_2$ nil to 8; $CH_4$ nil to 5; $H_2O$ nil to 5; A nil to 4; $N_2$ nil to 20; and $NH_3$ nil to trace.

At least a portion of, and preferably all of the cleaned and purified stream of synthesis gas from the first train is mixed with from about 0 to 100 volume % of the $H_2$-rich gas stream from the first train and at least a portion of, and preferably all of the $H_2$-rich gas stream from the second train to produce the cleaned and purified synthesis-gas stream having an $H_2$/CO mole ratio in the range of about 2 to 12. That portion of the cleaned and purified stream of synthesis gas from the first train which is not used to make said product gas may be recycled to the synthesis gas generator. Similarly, a portion of said product gas stream may be optionally recycled to the reaction zone of the synthesis gas generator.

In one embodiment of the subject invention, clean purified methanol synthesis gas is produced having a mole ratio $H_2$/CO in the range of about 2 to 4 by the previously described process steps. By conventional catalytic steps the synthesis gas may be converted into methanol.

The equilibrium exothermic reaction of carbon oxides and hydrogen to methanol, as shown in Equations II and III below, is favored by low temperature and high pressure. However, elevated tempertures may be necessary with some catalysts to obtain commercially adequate reaction rates.

$$CO + 2H_2 \rightarrow CH_3OH \qquad II$$

$$CO_2 + 3H_2 \rightarrow CH_3OH \qquad III$$

Conventional high-pressure methanol processes operate at temperatures in the range of about 650° to 750° F, at pressures in the range of about 250 to 350 atm. and with zinc-oxide/chromium-oxide catalysts.

Conventional low- and intermediate-pressure methanol processes operate at temperatures in the range of about 400° to 660° F., such as 440°-520° F.; at pressures in the range of about 40 to 250 atm., such as 40 to 150, and with catalysts composed largely of copper oxide with a lesser amount of zinc oxide and either chrome or aluminum oxides. The proportions of these three oxides are 30 to 60%, 20 to 40%, and 5 to 20%, respectively. Durability and thermal stability of the catalyst may be improved by the addition of manganese or vanadium. Methanol catalysts may be prepared by alkaline precipitation from nitric-acid solution, followed by drying, calcining, and pelletizing. Space velocities may range from about 10,000 to 40,000 hr$^{-1}$. Contact times are below 1.0 second. The rate of methanol formation is from about 0.3 to 2.0 kg/liter of catalyst/hr.

Optionally, the gaseous feed to the methanol converter may contain about 2 to 12 mole % of $CO_2$. For example, the mole ratio, $H_2/(2CO+3CO_2)$, in the feed gas stream to the methanol converter may be less than 1.05 and greater then 1.01. The presence of some $CO_2$ reduces the cost of the prior gas purification step. Further, the greater molar specific heat of the $CO_2$ relative to CO and the lower heat of reaction of the $CO_2$ provide a more uniform temperature control in the methanol reactor. The presence of $CO_2$ appears to be beneficial in repressing the formation of dimethyl ether.

Each mole of fresh methanol synthesis gas may be mixed with 0 to 10 moles of unconverted recycle gas from the methanol converter, i.e. 3 to 8 moles of recycle gas per mole of fresh methanol synthesis gas. A steam-turbine-driven circulating compressor may be used to compress and to circulate a mixture comprising the fresh methanol synthesis gas and the recycle gas. The working fluid for the turbine, i.e. steam, may be obtained from the main syngas cooler following the gas generator.

The feed-gas mixture to the methanol converter is preferably preheated by indirect heat exchange with the gaseous effluent stream departing from the methanol converter at a temperature in the range of about 500° to 800° F. and at a pressure in the range of about 20 to 450 atm., preferably at the pressure in the synthesis gas generator less ordinary drop in the lines and equipment. The effluent stream from the methanol reactor may have the following principal ingredients, in mole %: $CH_3OH$ 5 to 15; CO 8 to 25; $H_2$ 40 to 80; $CO_2$ 3 to 12; $H_2O$ 0.5 to 15; and $(CH_3)_2O$ .05 to 0.6. Minor amounts of other alcohols, aldehyes, and ketones may be present.

Futher cooling of the effluent gas stream in air and water coolers may be effected to condense crude methanol and water. This condensate flows to a separation zone in which uncondensed unreacted gases, i.e. $H_2$, $CO_2$, $CH_4$, $N_2$, A are separated, for example by flashing, and recycled to the gas compressor, with the exception of any purge stream. The crude methanol is purified by fractional distillation. Impurities including low-boiling compounds, principally dimethyl ether and higher alcohols, may be withdrawn from the distillation zone and optionally may be disposed as a waste stream or be used by recycling to the gas generator as a portion of the feed. Advantageously, these waste streams contain combined oxygen and therefore reduce the free-oxygen gas required for a given level of soot production. A portion of the product methanol may be introduced into one or both gas-purification zones in the first and second trains, as make-up solvent absorbent.

In the following embodiment of the subject invention, first methanol synthesis gas having a mole ratio $H_2/CO$ in the range of about 2 to 4 is made by the previously described process steps, concurrently with the CO-rich gas stream (or preferably substantially pure carbon monoxide). Crude methanol is then prepared in the manner previously described and purified. Although unpurified methanol and the CO-rich gas stream may be reacted to produce crude acetic acid, it is preferable to react purified methanol with substantially pure carbon monoxide in order to increase the reaction rate and to improve the selectivity.

Theoretically, one mole of carbon monoxide per mole of methanol is necessary to produce one mole of acetic acid, as shown in Equation IV below. The reaction is mildly exothermic; and, in practice, excess carbon monoxide is required, i.e. about 22%.

$$CH_3OH + CO \rightarrow CH_3COOH \qquad IV$$

Catalysts are commercially available for carbonylation reactions to produce acetic acid at high or low pressure, by either liquid- or vapor-phase reaction.

High-pressure carbonylation reactions for the preparation of crude acetic acid may take place at a temperature in the range of about 170° to 320° C., such as 200°-250° C., and at a pressure in the range of about 15 to 700 atmospheres, such as 150 to 315 atmospheres.

Suitable commercially-available high-temperature carbonylation catalysts for the preparation of acetic acid often comprise two main compounds. One component is a carbonyl-forming metal of the iron group, i.e. Fe, Co, or Ni in the form of a salt i.e. acetate. The other component is a halogen i.e. I, Br, or Cl as a free halogen or a halogen compound. For example, CoI or a mixture of cobalt acetate with an iodine compound are suitable catalysts. A contact time of about 2-3 minutes may be required to obtain 50-65% conversion of methanol by vapor-phase reaction at high pressure. Liquid phase reaction at about 180° C at 258 atm. may take about 3 hrs., for about 51% conversion. Water is used as a solvent or diluent, and it increases the methanol conversion while suppressing the production of methyl acetate. For example, about 30-40 wt. % of water may be present in the reaction zone.

Carbonylation reactions, for the preparation of crude acetic acid by reacting together methanol and carbon monoxide-rich gas or preferably substantially pure CO, may take place at a temperature in the range of about 150 to 200° C. and at a pressure in the range of about 34 to 680 atm., for liquid phase. For 50% conversion of the methanol, the reaction time is about 40-200 minutes. A temperature in the range of about 200° to 300° C. and a pressure in the range of about 1 to 10 atm. may be used for vapor-phase reaction.

Suitable commercially available low-temperature carbonylation catalysts for the preparation of acetic acid comprise the following combination of ingredients: (1) noble metal catalyst, (2) catalyst promoter, and (3) dispersant or carrier. The noble metal active catalyst may be selected from the group consisting of rhodium, palladium, platinum, iridium, osmium, or ruthenium, in the form of an oxide, organometallic compound, salt, or a coordination compound, consisting of one of said noble metals, CO, a halide, such as chloride, bromide, or iodide, and a suitable amine, organo phosphine, organoarsine, or organostibine ligand. The catalyst promoter may consist of a halogen or halogen compound. The dispersant in liquid-phase processes is a solvent for the metal catalytic component i.e. mixture of acetic acid and water. In vapor-phase processes the same noble-metal compound and promoter as previously described are dispersed on a carrier, i.e. pumice, alumina, activated carbon, or silica.

For example, a typical low-pressure catalyst for the liquid-phase process may comprise $10^{-2}$ to $10^{-4}$ mol/liter of chlorocarbonyl-bis-triphenolphosphine rhodium, and $10^{-4}$ to 2 mol/liter of methyl iodide dissolved in a mixture of acetic acid and water. The ratio of atoms of halogen in the promoter to atoms of noble metal in the catalyst is preferably in the range of about 3 to 300.

In the low-pressure process for the production of glacial acetic acid by liquid-phase carbonylation, at least a portion of the pure methanol as produced previously is mixed in a reactor surge tank with recovered recycled unreacted methanol, catalyst, catalyst promoter, acetic acid solvent for the catalyst, methyl acetate, and water. The mixture is then pumped into a carbonylation reactor, along with substantially pure carbon monoxide, in which the carbonylation reaction takes place at a temperature, for example of 200° C. and at a pressure of about 35 atmospheres. The gaseous product is cooled and sent to a separation zone in which uncondensed gases and condensate are separated. The uncondensed gas may be scrubbed with fresh methanol to recover the entrained methanol, methyl acetate, and methyl iodide for recycle to the reactor surge tank. Optionally, the residual off-gas may be recycled to the gas generator, or to the water-gas shift converter, or vented. The liquid product from the reactor and the condensate are sent to a separation zone, i.e. distillation zone, in which at a pressure of about 1–3 atm. the low-boiling constituents, such as methanol, methyl acetate, and methyl iodide, are separated and recycled to the reactor surge tank, along with recovered rhodium compound catalyst dissolved in acetic acid, and with water which may be recovered by azeotropically dehydrating acetic acid. Glacial acetic acid product is also separated along with a bottoms stream comprising propionic acid and heavy ends.

Advantageously, the waste bottoms stream of propionic acid and heavy ends, as well as any off-gas stream that is not purged may be recylced to the gas generator as a portion of the feed. By this means the environment is not polluted.

DESCRIPTION OF THE DRAWING

Figure 1A:
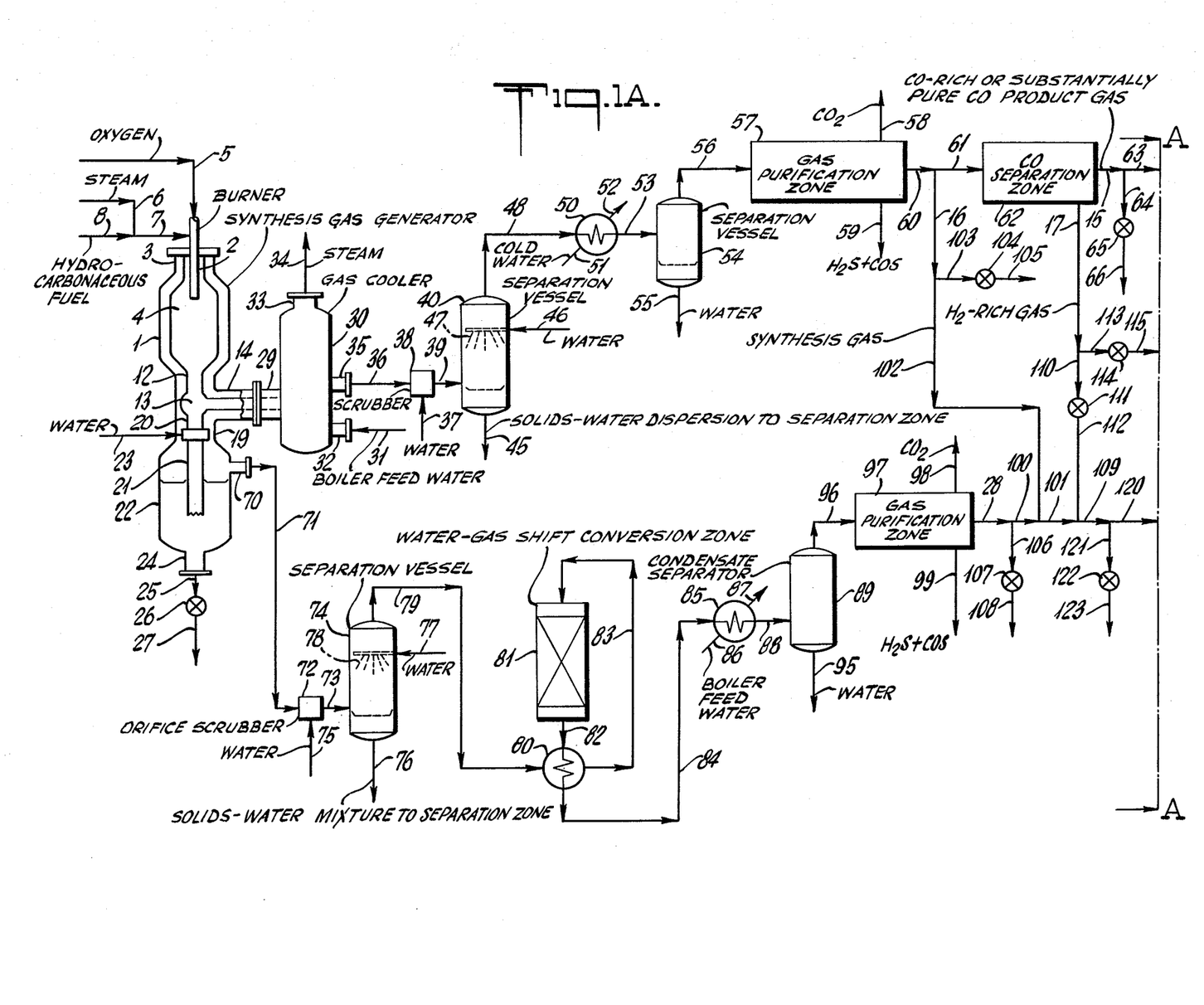
FIG. 1A is a schematic representation of a preferred embodiment of the process for simultaneously making a product stream of clean and purified synthesis gas having a mole ration $H_2/CO$ in the range of about 2 to 12, and a separate product stream of CO-rich gas and preferably substantially pure CO.
Figure 1B:
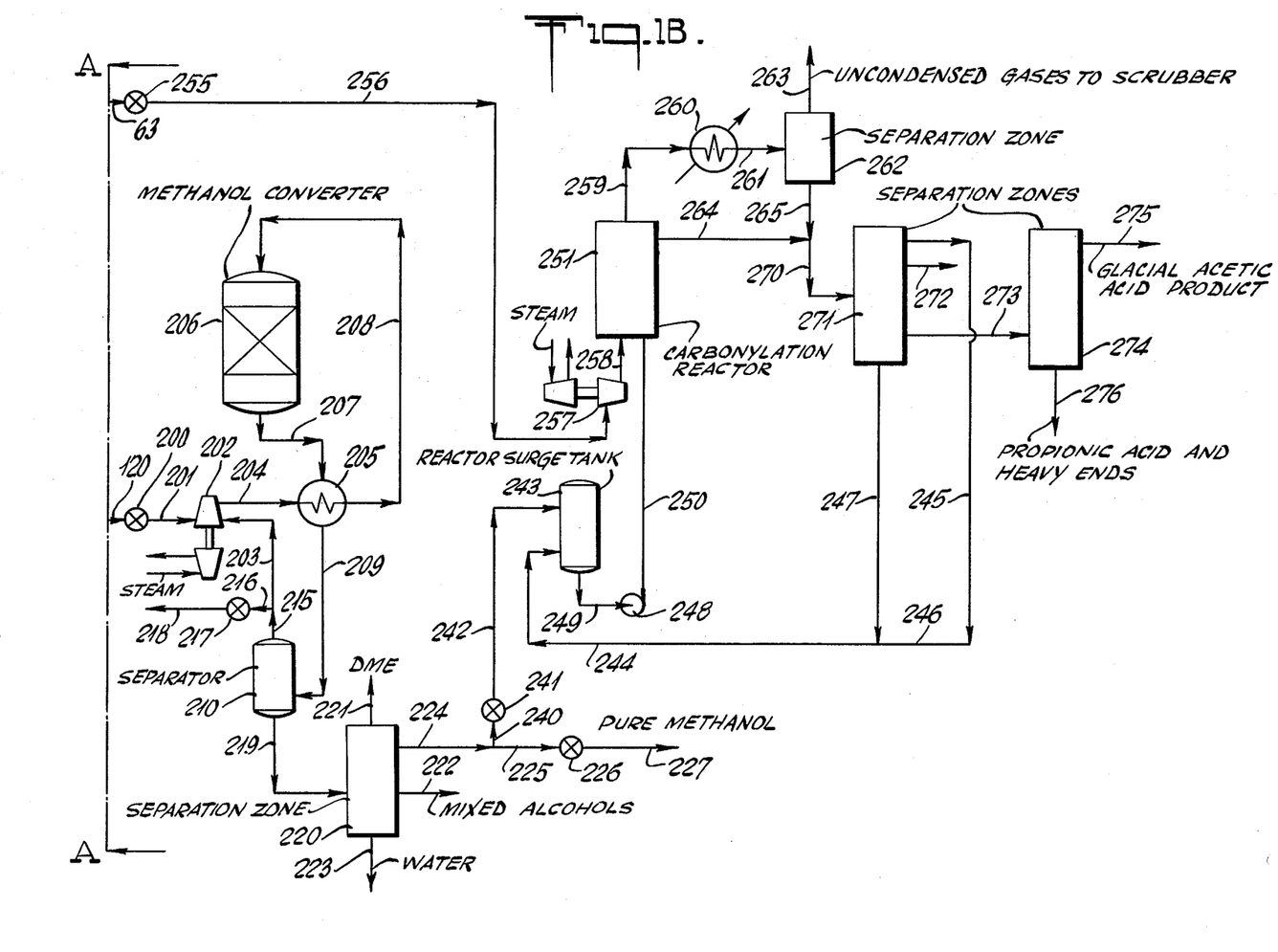
FIG. 1B as shown to the right of line A—A is a schematic representation of another embodiment of the process, in which pure methanol is produced from a product stream of methanol synthesis gas made by the subject process. Optionally, at least a portion of said pure methanol may be then reacted with at least a portion of the substantially pure carbon monoxide stream to produce acetic acid.

A more complete understanding of the invention may be had by reference to the accompanying schematic drawing. A preferred embodiment of the process of this invention is illustrated by that portion of the drawing, FIG. IA, to the left of line A—A. Other embodiments are shown in FIG. 1B to the right of line A—A. It is not intended to limit the continuous process illustrated to the particular apparatus and materials described.

With reference to the FIG. 1A, unpacked, free-flow noncatalytic refractory lined synthesis gas generator 1, as previously described has an annulus-type burner 2 mounted in its upper inlet port 3 along the vertical axis. The feed streams are introduced into the reaction zone 4 of the gas generator by way of burner 2. They include an oxygen stream which passes through line 5, and the central conduit (not shown) of the burner, a stream of steam which passes through lines 6 and 7, and a stream of hydrocarbonaceous fuel which passes through lines 8 and 7. The latter two streams are mixed together in line 7 and the mixture is then passed through the annulus passage (not shown) in burner 2.

The effluent stream of raw synthesis gas leaves the reaction zone and passes through exit passage 12 and directly into an insulated chamber 13 where the effluent gas stream is split into two gas streams. One split stream of raw synthesis gas passes through insulated transfer line 14 into the first train of process steps which ends with the production of a stream of CO-rich gas or substantially pure CO product gas in line 15, a stream of clean and purified synthesis gas in line 16, and a $H_2$-rich gas stream in line 17. The second split stream of raw synthesis gas passes directly into a second train of process steps by way of line 20, dip tube 21, and quench tank 22. Water enters quench tank 22 by way of line 23; and a water slurry of solid particles of carbon and ash are periodically removed by way of exit port 24, line 25, valve 26, and line 27 at the bottom of the quench tank. This slurry removal may be done by means of a lock hopper system (not shown). The water slurry is sent to a water separator (not shown) where a stream of clarified water is separated and recycled to quench tank 22. The second train terminates with the production of a clean and purified $H_2$-rich gas stream in line 28. The product gas stream of cleaned and purified synthesis gas may be prepared by mixing together in desired proportions streams 16, 17, and 28 in the manner to be more fully described.

Returning now to the first split stream of raw synthesis gas in transfer line 14, this gas stream is passed through inlet 29 of gas cooler 30 where it is cooled by indirect heat exchange with a stream of boiler feed water from line 31. The boiler feed water passes through inlet 32 and leaves as steam through outlet 33 and line 34. The cooled raw synthesis gas leaves through outlet 35, line 36, and is contacted with water from line 37 in orifice or venturi scrubber 38. Any entrained solids i.e. particulate carbon and ash are thereby scrubbed from the raw synthesis gas and pass with the water through line 39 into separation vessel 40. A mixture of solid particles and water is removed through line 45 near the bottom of vessel 40 and is sent to a separator (not shown) where clarified water is separated and recycled to lines 37 and 46. Additional gas scrubbing may be achieved, for example, by passing the stream of synthesis gas through water spray 47 prior to leaving vessel 40 through line 48.

The cleaned synthesis gas is cooled below the dew point in heat exchanger 50 by indirect heat exchange with cold water entering through line 51 and leaving by line 52. The cooled stream passes through line 53 into separation vessel 54 where the condensed water is removed at the bottom by way of line 55 and the gas stream leaves through line 56 at the top. The cleaned synthesis gas stream is then purified in gas purification zone 57. Gaseous impurities are separated and for example $CO_2$ leaves by way of line 58, and a stream of $H_2S$ + COS passes through line 59 into a Claus unit (not shown) for conversion into sulfur.

The cleaned and purified synthesis gas stream in line 60 is then split into two streams 61 and 16. The stream of synthesis gas in line 61 is subjected to further treatment in carbon monoxide separation zone 62. At least a portion and preferably all of the CO-rich gas or substantially pure carbon monoxide product gas which exits through line 15 and 63 may be used in organic synthesis. The remainder may be exported through line 64, valve 65, and line 66. As previously noted, the $H_2$-rich gas stream leaves CO separation zone 62 by way of line 17.

Returning now to the second train, after being quenched in water the cooled raw synthesis gas stream substantially saturated with water passes through outlet 70, line 71, orifice or venturi scrubber 72, and line 73 into separation vessel 74. Scrubbing water in line 75 is passed into orifice scrubber 72 where further cleaning of the synthesis gas stream may take place. A mixture of solids i.e. particulate carbon and ash, and water leave vessel 74 near the bottom through line 76 and are then introduced into a separation zone (not shown) where clarified water is produced. The clarified water is recycled as the scrubbing fluid in lines 75 and 77. The gas stream may be sprayed with water from spray 78 and leaves vessel 74 near the top through line 79.

The cleaned synthesis gas stream saturated with water is preheated in heat exchanger 80 by indirect heat exchange with the shifted stream of synthesis gas leaving catalytic water-gas shift conversion zone 81 through line 82. The feed stream enters shift conversion zone 81 through line 83, and CO and $H_2O$ in the process gas stream react therein to produce $H_2 + CO_2$. The resulting clean $H_2$-rich gas stream is cooled in heat exchanger 80 and then passed through line 84 into gas cooler 85 where the temperature of gas stream is dropped below the dew point by indirect heat exchange with water. For example, boiler feed water in line 86 may be preheated in heat exchanger 85, passed through line 87, and then introduced into gas cooler 30 by way of line 31 where it is converted into stream. The cooled $H_2$-rich gas stream is passed through line 88 into condensate separator 89 where condensed water is drawn off at the bottom through line 95 and clean $H_2$-rich gas exits through line 96 at the top. In gas purification zone 97, the $H_2$-rich gas stream is separated from unwanted gaseous impurities. For example, a stream of $CO_2$ is removed through line 98, and a stream of $H_2S + COS$ is removed through line 99 and sent to a Claus unit (not shown) for the production of sulfur. A clean $H_2$-rich gas stream is removed from gas purification zone 97 through line 28. At least a portion, and preferably all of the $H_2$-rich gas stream in line 28 is passed through line 100 into line 101 where it is mixed with at least a portion, and preferably all of the stream of cleaned and purified synthesis gas from lines 16, and 102 from the first train. Any remaining portion of cleaned and purified synthesis gas from line 16 may be exported through line 103, valve 104, and line 105. Any remaining portion of the $H_2$-rich gas stream from line 28 may be exported through line 106, valve 107, and line 108. The synthesis gas stream in line 101 is passed into line 109 where it may be mixed with 0 to 100 volume % of the $H_2$-rich gas from lines 17, 110, valve 111, and line 112. Any remaining portion of the $H_2$-rich gas in line 17 may be exported through line 113, valve 114, and line 115. The cleaned and purified synthesis gas product stream in line 109 has a $H_2/CO$ mole ratio in the range of about 2 to 12. At least a portion and preferably all of this gas stream may be passed through line 120 for use in organic synthesis. Any remaining portion of the synthesis gas stream from line 109 may be passed through line 121, valve 122, and line 123 to export, or recycle to the gas generator.

In another embodiment shown in FIG. 1B, pure methanol is made by the catalytic reaction of at least a portion of cleaned and purified product stream of methanol synthesis gas from line 120. The process steps are shown to the right of section line A—A in the drawing. The process gas stream from line 120 is passed through valve 200, and line 201 into steam turbocompressor-circulator 202 along with unconverted recycle gases from line 203. The compressed gases in line 204 are then preheated in heat exchanger 205 by indirect heat exchange with the hot impure methanol vapor leaving catalytic methanol reactor 206 by way of line 207. The preheated methanol synthesis gas stream in line 208 is passed through methanol reactor 206 where reaction between $H_2$ and carbonix oxides take place to produce crude methanol. After being partially cooled in heat exchanger 205, the methanol reaction products pass through line 209 into separation zone 210 where the unreacted gases are separated from the crude methanol. The unreacted gases are passed through lines 215 and 203 into recycle compressor 202, except for the purge gas which is passed through line 216, valve 217, and line 218. The crude methanol in line 219 is introduced into the purification zone 220 where impurities are removed, for example, by distillation. Dimethyl ether may be removed through line 221, mixed alcohols through line 222, and water through line 223. Pure methanol may be drawn off through lines 224, 225, valve 226, and line 227. Optionally, by-product oxygen-containing organic compounds from lines 221, 222, and 218 may be recycled to the gas generator as a portion of the fuel and to reduce the free-oxygen requirements for a given level of soot production.

In still another embodiment of the invention a raw stream of acetic acid is prepared by the low pressure liquid-phase catalytic carbonylation reaction between the pure methanol and the substantially pure carbon monoxide made previously in the subject process. In such case, at least a portion of the pure methanol in line 224 is passed through line 240, valve 241, and line 242 into reactor surge tank 243 and mixed with a mixture of recycle materials from line 244. Recycle stream 244 comprises a mixture of methanol, methyl acetate, and methyl iodide from lines 245 and 246 and a rhodium catalyst compound i.e, $Rh(CO)[P(C_6H_5)_3]_2 Cl$ dissolved in a mixture of acetic acid and water from line 247.

By means of pump 248, the reactant mixture in tank 243 is pumped through lines 249 and 250 into vertical carbonylation reactor 251. Simultaneously, at least a portion of the substantially pure CO gas stream in line 63 is passed into carbonylation reactor 251 by way of valve 255, line 256, optionally steam turbocompressor 257, and line 258. In reactor 251, methanol and CO react to produce acetic acid. An overhead gaseous stream is passed through line 259, cooled in heat exchanger 260, and passed through line 261 into separator 262. The uncondensed gases in line 263 are scrubbed with fresh methanol in a tower (not shown) to recover entrained methanol, methyl acetate and methyl iodide for recycle to the reactor surge tank 243. Residual off-gas from the scrubber may be recycled to the gas generator or vented.

The liquid product from the reactor in line 264 and the condensate from line 265 are passed through line 270 into separation zone 271. For example, by distillation, the low boiling constituents comprising a mixture of methanol, methyl acetate, and methyl iodide may be separated and leve by way of line 245; water is removed through line 272; recovered rhodium compound catalyst dissolved in acetic acid is removed through line 247; and impure acetic acid is removed through line 273 and fed into separation zone 274. Glacial acetic acid is recovered as a distillate from line 275. Propionic acid and heavier components leave through line 276 and may be recycled to the gas generator as a portion of the fuel.

EXAMPLE

The following example illustrates a preferred embodiment of the process of this invention as shown in the drawing pertaining to the simultaneous production of a clean purified stream of methanol synthesis gas and a stream of substantially pure carbon monoxide. While preferred modes of operation are illustrated, the Example should not be construed as limiting the scope of the invention. The process is continuous and the flow rates are specified on an hourly basis for all streams of materials.

162,356 lbs. of a vacuum resid having a gravity of 2.0 degrees API and an Ultimate Analysis in weight percent as follows: C 83.45, H 10.10, N 0.35, S 5.50, and 0 0.60 are mixed with 2765 pounds of recycled unreacted particulate carbon recovered downstream in the process to produce a pumpable dispersion of particulate carbon and petroleum oil. The oil-carbon dispersion, referred to in line 8 of the drawing as hydrocarbonaceous fuel, is pumped through a heater where it is brought up to a temperature of 540° F. and a pressure of 1165 psig. The dispersion is then mixed with a stream of 64,942 lbs. of steam at a temperature of 574° F. and a pressure of 1165 psig. from line 6.

The oil-carbon-steam mixture is passed through the annulus of an annulus-type burner which is located in the upper end of a conventional vertical refractory lined freeflow noncatalytic unpacked synthesis gas generator.

Simultaneously, a stream of 171,033 lbs. of substantially pure oxygen i.e., 99.5 mole % $O_2$ from line 5 is passed through the center passage of the burner. The two streams impinge, mix and the partial oxidation and other related reactions then take place in the reaction zone of the gas generator.

A stream of 8.69 million standard cubic feet (SCF measured at 60° F., 14.7 psia) of raw synthesis gas leave the reaction zone of the gas generator at a temperature of 2596° F. and a pressure of 1050 psig. The composition of the raw synthesis gas at the exit 12 from reaction zone 4 is shown in Column 1 of Table I. About 2765 lbs. of unreacted carbon plus ash are entrained in the raw synthesis gas.

The raw effluent gas stream leaving the reaction zone is split into two streams at 13: 5.65 million SCF of raw synthesis gas are processed in a first train; and the remainder, 3.04 million SCF of raw synthesis gas are simultaneously processed in the secnd train.

The composition of the raw fuel gas leaving gas cooler 30 in line 36 is shown in Cloumn 2 of Table I. After substantially all of the entrained carbon and ash are scrubbed from the raw synthesis gas and the gas stream is cooled below the dew point to condense out substantially all of the water, the composition of the raw synthesis gas stream in line 56 is shown in Column 3 of Table I.

Gaseous impurities including $CO_2$, $H_2S$, and COS are removed from the stream of cleaned raw synthesis gas to produce 4.75 million SCF of an intermediate stream of cleaned and purified synthesis gas in line 60 having the composition shown in Column 4 of Table I. The intermediate stream of cleaned and purified synthesis gas is split into the following two streams: (a) a stream of 2.51 million SCF which is processed in a CO-separation zone, and (b) the remainder consisting of a stream of 2.24 million SCF which is mixed with $H_2$-rich gas, to be further described.

A stream of 1.14 million SCF of substantially pure CO in line 15 is produced in the CO separation zone having the composition shown in Column 5 of Table I. Also, a stream of 1.37 million SCF of $H_2$-rich gas in line 17 is produced in the CO separation zone having the composition shown in Column 6 of Table I.

Returning now to the second split stream of raw synthesis gas which comprises the remainder of the stream of raw synthesis gas leaving the reaction zone. By passing all of the raw synthesis gas from the rection zone through a passage of reduced diameter, its rate of flow may be accelerated and the velocity of the solid particles i.e. carbon and ash entrained in the gas stream may be increased. Accordingly, a large proportion of the solid particles may be entrained in the second split stream of raw synthesis gas which is directly quenched in water which is contained in a quench tank located below the gas generator. The first split stream of raw synthesis gas is diverted and processed in the first train, as described previously. The actual split between the two trains may be controlled by back pressure valves in each line.

The stream of 7.07 million SCF of raw synthesis gas in line 79 is saturated with water as the result of being quenched and scrubbed with water and has the composition shown in Column 7 of Table I. 7.07 million SCF of effluent gas leaving the catalytic water-gas shift converts in line 82 has the composition shown in Column 8 of Table I. After being cooled by indirect heat exchange below the dew point, the gas stream in line 96 has the composition shown in Column 9 of Table I. This gas stream is then purified in a gas purification zone to produce 3.34 million SCF of clean purified $H_2$-rich gas in line 28 having the composition shown in Column 10 of Table I.

All of the substantially dry intermediate stream of clean and purified synthesis gas in line 16 in the amount of 2.24 million SCF are mixed with all of the substantially dry $H_2$-rich gas stream in line 28 in the amount of 3.34 million SCF to produce the gas stream in line 101 having the composition shown in Column 11 of Table I. All of the gas stream in line 101 is then mixed with all of the $H_2$-rich gas stream from line 17 in the amount of 1.37 million SCF to produce a substantially dry product stream of 6.95 million SCF of cleaned and purified synthesis gas in line 109 having the composition in Column 12 of Table I. This is the proper gas composition for mixing with unconverted recycle gas from a catalytic methanol convertor to produce a feed gas for converting into crude methanol. Pure methanol may be produced by purification and reacted in a catalytic carbonylation reactor with at least a portion of the stream of substantially pure carbon monoxide from stream 15 to produce crude acetic acid. Glacial acetic acid may be then produced by purification.

The process of the invention has been described generally and by examples with reference to a hydrocarbonaceous fuel, synthesis gas, and H₂-rich gas of particular compositions for purposes of clarity and illustration only. It will be apparent to those skilled in the art from the foregoing that various modifications of the process and materials disclosed herein can be made without departure from the spirit of the invention.

with from 0 to 100% of said H₂-rich gas stream from (5) and at least a portion of said cleaned and pruified H₂-rich gas stream from (8) to produce said product stream of cleaned and purified synthesis gas.

2. The process of claim 1 in which the effluent gas stream from the reaction zone in step (1) and the

TABLE 1

| Column No. | 1 | 2 | 3 | 4 | 5 | 6 | 7 | 8 | 9 | 10 | 11 | 12 |
|---|---|---|---|---|---|---|---|---|---|---|---|---|
| Drawing Reference No. | 12 | 36 | 56 | 60 | 15 | 17 | 79 | 82 | 96 | 28 | 101 | 109 |
| GAS COMPOSITION | | | | | | | | | | | | |
| COMPOSITION, MOLE % | | | | | | | | | | | | |
| CO | 44.56 | 44.56 | 49.25 | 52.15 | 97.88 | 13.74 | 19.16 | 0.80 | 1.39 | 1.66 | 22.01 | 20.38 |
| $H_2$ | 39.87 | 39.87 | 44.06 | 47.20 | 0.25 | 86.17 | 17.14 | 35.51 | 61.96 | 74.90 | 63.81 | 68.22 |
| $CO_2$ | 4.27 | 4.27 | 4.72 | — | — | — | 1.83 | 20.23 | 35.31 | 22.95 | 13.73 | 11.03 |
| $H_2O$ | 9.52 | 9.52 | — | — | — | — | 61.10 | 42.69 | — | — | — | — |
| $CH_4$ | 0.36 | 0.36 | 0.40 | 0.40 | 1.40 | 0.02 | 0.15 | 0.16 | 0.27 | 0.31 | 0.24 | 0.19 |
| A | 0.12 | 0.12 | 0.13 | 0.14 | 0.22 | 0.02 | 0.05 | 0.05 | 0.09 | 0.10 | 0.13 | 0.11 |
| $N_2$ | 0.09 | 0.09 | 0.10 | 0.11 | 0.25 | 0.05 | 0.04 | 0.04 | 0.07 | 0.08 | 0.08 | 0.07 |
| $H_2S$ | 1.15 | 1.15 | 1.27 | — | — | — | 0.50 | 0.52 | 0.91 | — | — | — |
| COS | 0.06 | 0.06 | 0.07 | — | — | — | 0.03 | — | — | — | — | — |

I claim

1. Process for the simultaneous production of a product stream of cleaned and purified synthesis gas and a CO-rich product-gas stream comprising:

(1) reacting a hydrocarbonaceous or oxygenated hydrocarbonaceous organic material with a free-oxygen containing gas, optionally in the presence of a temperature moderator in the reaction zone of a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, solid particles of carbon and ash and at least one gas from the group consisting of $CO_2$, $H_2S$, COS, $CH_4$, $NH_3$, $N_2$, and A;

(2) splitting the effluent gas stream from (1) into first and second gas streams, and simultaneously processing said first and second gas streams in separate first and second trains;

(3) cooling said first gas stream from (2) in said first train by indirect heat exchange in a separate heat-exchange zone; cleaning to remove any entrained solids, and removing water;

(4) purifying at least a portion of the gas stream from (3) in a first gas-purification zone and separating therefrom at least one gas from the group $CO_2$, $H_2S$, COS, $CH_4$, and $NH_3$, to produce a cleaned and purified stream of synthesis gas free-from gaseous sulfur compounds;

(5) dividing the cleaned and purified stream of synthesis gas from (4) into two streams and introducing the first of these streams into a CO-separation zone from which said product stream of CO-rich gas and a separte stream of $H_2$-rich gas are removed;

(6) cooling and cleaning said second gas stream from (2) by direct contact with water thereby removing the solid particles entrained therein and increasing the $H_2O$/CO mole ratio of said gas stream to a value in the range of about 2 to 5;

(7) reacting together CO and $H_2O$ in the gas streams from (6) in a water-gas shift conversion zone to produce a $H_2$-rich gas stream;

(8) removing $H_2O$ and purifying at least a portion of the $H_2$-rich gas stream from (7) in a second-gas purification zone and separating therefrom at lest one gas from the group $CO_2$, $H_2S$, COS, $CH_4$, and $NH_3$ to produce a cleaned and purified $H_2$-rich gas stream free from gaseous sulfur compounds; and (9) mixing at least a portion of said second divided stream of cleaned and purified synthesis gas from (5) cleaned and purified stream of synthesis gas from step (4) have a mole ratio $H_2$/CO in the range of about 0.5 to 1.9, and the product stream of cleaned and purified synthesis gas has a mole ratio $H_2$/CO in the range of about 2 to 12.

3. The process of claim 2 in which said product stream of cleaned and purified synthesis gas is methanol synthesis gas having a $H_2$/CO mole ratio in the range of about 2-4.

4. The process of claim 1 in which said product stream of cleaned and purified synthesis gas is delivered at a pressure which is about that in the synthesis gas generator less ordinary drop in the lines and equipment.

5. The process of claim 1 in which the following gas streams contain substantially no water: (a) the purified stream of synthesis gas from step (4), (b) the cleaned and purified $H_2$-rich gas streams from steps (5) and (8), and (c) the CO-rich gas stream from step (5).

6. The process of claim 1 in which said product stream of CO-rich gas is substantially pure CO containing about 95–99 mole percent CO.

7. The process of claim 1 in which said second split stream from step (2) contains about 20 to 70 volume percent of the effluent gas stream from step (1), the remainder of which comprising said first split stream.

8. The process of claim 1 in which the cleaned and purified stream of synthesis gas is divided in step (5) into said first stream containing 5 to 50 volume percent and into said second divided stream contaning the remainder of said cleaned and purified stream of synthesis gas.

9. The process of claim 1 provided with the additional step of preheating the second gas stream from step (6) to a temperature in the range of about 600° to 850° F. and reacting said gas stream in step (7) while in contact with a water-gas shift catalyst comprising iron oxide — chromium oxide promoted by 1 to 15 weight percent of an oxide of a metal selected from the group, K, Th, U, Be, and Sb.

10. The process of claim 1 in which said second gas stream from step (6) is reacted in step (7) while in contact with a water-gas shift catalyst which comprises a Co-Mo catalyst comprising in weight percent CoO 2–5, $MoO_3$ 8–16, MgO nil-20, and $Al_2O_3$ 59–85.

11. The process of claim 1 in which said second gas stream from step (6) is reacted in step (7) while in contact with a water-gas shift catalyst which comprises copper and zinc salts or oxides in the weight ratio of about 3 parts by weight zinc and 1 part copper.

12. The process of claim 1 in which said free-oxygen containing gas is substantially pure oxygen (95 mole percent $O_2$ or more).

13. The process of claim 1 in which said hydrocarbonaceous feedstock is selected from the group consisting of liquified petroleum gas, petroleum distillates and residua, naphtha, gas oil, residual fuel, reduced crude, whole crude, asphalt, coal tar, coal-derived oil, shale oil, tarsand oil, and pumpable slurries of coal, particulate carbon, and petroleum cole in water or in liquid hydrocarbon fuel, and mixtures thereof.

14. The process of claim 1 in which said hydrocarbonaceous feedstock is selected from the group consisting of methane, propane, natural gas, water-gas, coke-oven gas, synthesis gas, refinery gas, and mixtures thereof.

15. The process of claim 1 in which said hydrocarbonaceous feedstocks are organic materials selected from the group consisting of carbohydrates, cellulosic materials, aldehydes, organic acids, alcohols, ketones, oxygenated fuel oil, waste liquids, and by-products from chemical processes containing oxygenated hydrocabonaceous organic materials, and mixtures thereof.

16. The process of claim 1 in which a portion of the gas stream from step (3), or a portion of the $H_2$-rich gas stream from step (7) after removal of water, or a portion of each of said gas streams by-pass said first and second gas purification zones in their respective lines; and mixing separately each by-pass gas stream with its related purified gas stream.

17. The process of claim 1 in which a portion of the $H_2$-rich gas stream from step (8), or a portion of the product stream of cleaned and purified synthesis gas from step (9), or a portion of each of said gas streams are recycled to the gas generator in step (1).

18. A process for producing substantially pure methanol and a by-product stream of CO-rich gas comprising:
(1) reacting a hydrocarbonaceous and oxygen-containing hydrocarbonaceous organic material with substantially pure oxygen optionally in the presence of $H_2O$ in a reaction zone of a free-flow noncatalytic partial oxidation gas generator at a temperature in the range of about 1300° to 3000° F and at a pressure in the range of about 1 to 250 atmospheres to produce an effluent gas stream comprising $H_2$, CO, $H_2O$, solid particles of carbon and ash and at least one gas from the group consisting of $CO_2$, $H_2S$, COS, $CH_4$, $NH_3$, $N_2$, and A; and wherein said effluent gas stream has a mole ratio $H_2/CO$ in the range of about 0.5 to 1.9;
(2) splitting the efflucent gas stream from (1) into first and second gas streams, wherein said second split stream contains about 20 to 70 volume % of the effluent gas stream from (1), and the remainder of which comprising said first split stream, and simultaneously processing said first and second gas streams in separate first and second trains;
(3) cooling said first gas stream from (2) in said first train by indirect heat exchange in a separate heat-exchange zone, cleaning to remove any entrained solids, and removing water;
(4) purifying at least a portion of the gas stream from (3) in a first gas-purification zone and separating therefrom at least one gas from the group $CO_2$, $H_2S$, COS, $CH_4$, and $NH_3$, to produce a cleaned and purified stream of synthesis gas free-from gaseous sulfur-compounds and having a mole ratio $H_2/CO$ in the range of about 0.5 to 1.9;
(5) dividing the cleaned and purified stream of synthesis gas from (4) into a first stream containing 5 to 50 volume percent and into a second stream containing the remainder of said cleaned and purified stream of synthesis gas, and introducing the first of these streams into a CO-separation zone from which said by-product stream of CO-rich gas and a separate stream of $H_2$-rich gas are removed;
(6) cooling and cleaning said second gas stream from (2) by direct contact with water thereby removing the solid particles entrained therein and increasing the $H_2O/CO$ mole ratio of said gas stream to a value in the range of about 2 to 5;
(7) reacting together CO and $H_2O$ in the gas stream from (6) in a water-gas shift conversion zone to produce a $H_2$-rich gas stream;
(8) removing $H_2O$ and purifying at least a portion of the $H_2$-rich gas stream from (7) in a second-gas purification zone and separating therefrom at least one gas from the group $CO_2$, $H_2S$, COS, $CH_4$, and $NH_3$ to produce a cleaned and purified $H_2$-rich gas steam freefrom gaseous sulfur-compounds;
(9) mixing at least a portion of said second divided stream of cleaned and purified synthesis gas from (5) with from 0 to 100% of said $H_2$-rich gas stream from (5) and at least a portion of said cleaned and purified $H_2$-rich gas stream from (8) to produce a stream of cleaned and purified methanol synthesis gas having a mole ratio $H_2/CO$ in the range of about 2–4;
(10) reacting at least a portion of said methanol synthesis gas in the presence of a methanol catalyst in a methanol-synthesis zone at a temperature in the range of about 400° to 750° F and at a pressure in the range of about 40 to 350 atm. to produce crude methanol, and purifying said crude methanol to oxygen-containing substantially pure methanol and by-product oxygen-contaning organic materials; and
(11) introducing at least a portion of said by-product oxygen-containing organic materials into the reaction zone of the partial oxidation gas generator in (1) as at least a portion of said oxygen-containing hydrocarbonaceous organic material.

19. The process of claim 18 in which said methanol catalyst comprises zinc oxide and chromium oxide, the temperature in said methanol-synthesis zone is in the range of about 650° to 750° F., and the pressure is in the range of about 250 to 350 atm.

20. The process of claim 18 in which said methanol catalyst comprises copper oxide, zinc oxide, chromium oxide or aluminum oxide, the temperature in said methanol-synthesis zone is in the range of about 400° to 660° F., and the pressure is in the range of about 40 to 250 atm.

21. The process of claim 18 in which the pressure in said methanol-synthesis zone is the same as that in the synthesis-gas generator less ordinary pressure drop in the lines and equipment.

22. The process of claim 18 in which at least a portion of said substantially pure methanol is used in said first and second gas-purification zones to absorb gaseous impurities from the gas streams.

23. The process of claim 18 in which the mole ratio $H_2 12CO + 3CO_2$ of the cleaned and purified methanol synthesis gas from step 9 is in the range of less than 1.05 and greater than 1.01.

24. A process for producing acetic acid comprising:
(1) reacting hydrocarbonaceous and oxygen-containing hydrocarbonaceous organic material with substantially pure oxygen optionally in the presence of $H_2O$ in a reaction zone of a free-flow noncatalytic partial-oxidation gas generator at a temperature in the range of about 1300° to 3000° F and at a pressure in the range of about 1 to 250 atmospheres to produce an effluent gas stream comprising $H_2$, CO, $H_2O$, solid particles of carbon and ash and at least one gas from the group consisting of $CO_2$, $H_2S$, COS, $CH_4$, $NH_3$, $N_2$, and A; and wherein said effluent gas stream has a mole ratio $H_2/CO$ in the range of about 0.5 to 1.9;
(2) splitting the effluent gas stream from (1) into first and second gas streams, wherein said second split stream contains about 20 to 70 volume % of the effluent gas stream from (1), and the remainder of which comprising said first split stream, and simultaneously processing said first and second gas streams in separate first and second trains;
(3) cooling said first gas stream from (2) in said first train by indirect heat exchange in a separate heat-exchange zone, cleaning to remove any entrained solids, and removing water;
(4) purifying at least a portion of the gas stream from (3) in a first gas-purification zone and separating therefrom at least one gas from the group $CO_2$, $H_2S$, COS, $CH_4$, and $NH_3$, to produce a cleaned and purified stream of synthesis gas free-from gaseous sulfur-compounds and having a mole ratio $H_2/CO$ in the range of about 0.5 to 1.9;
(5) dividing the cleaned and purified stream of synthesis gas from (4) into a first stream containing 5 to 50 volume percent and into a second stream containing the remainder of said cleaned and purified stream of synthesis gas, and introducing the first of these stream into a CO-separation zone from which a stream of substantially pure CO gas and a separate stream of $H_2$-rich gas are removed;
(6) cooling and cleaning said second gas stream from (2) by direct contact with water thereby removing the solid particles entrained therein and increasing the $H_2O/CO$ mole ratio of said gas stream to a value in the range of about 2 to 5;
(7) reacting together CO and $H_2O$ in the gas stream from (6) in a water-gas shift conversion zone to produce a $H_2$-rich gas stream;
(8) removing $H_2O$ and purifying at least a portion of the $H_2$-rich gas stream from (7) in a second-gas purification zone and separating therefrom at least one gas from the group $CO_2$, $H_2S$, COS, $CH_4$, and $NH_3$ to produce a cleaned and purified $H_2$-rich gas stream free-form gaseous sulfur-compunds;
(9) mixing at least a portion of said second divided stream of cleaned and purified synthesis gas from (5) with from 0 to 100% of said $H_2$-rich gas stream from (5) and at least a portion of said cleaned and purified $H_2$-rich gas stream from (8) to produce a stream of cleaned and purified methanol synthesis gas having a mole ratio $H_2/CO$ in the range of about 2–4;
(10) reacting at least a portion of said methanol synthesis gas in the presence of a methanol catalyst in a methanol-synthesis zone at a temperature in the range of about 400° to 750° F and at a pressure in the range of about 40 to 350 atm. to produce crude methanol, and purifying said crude methanol to produce substantially pure methanol and by-product oxygen-containing organic materials;
(11) reacting at least a portion of said substantially pure methanol with at least a portion of said substantially pure carbon monoxide in the presence of a carbonylation catalyst in an acetic acid-synthesis zone at a temperature in the range of about 302° to 608° F and at a pressure in the range of about 1 to 700 atmospheres to produce impure acetic acid, and purifying said impure acetic acid to produce substantially pure acetic acid and by-product oxygen-containing organic materials; and
(12) introducing at least a portion of said by-product oxygen-containing organic materials from (10), or (11), or both into the reaction zone of the partial oxidation gas generator in (1) as at least a portion of said oxygen-containing hydrocarbonaceous organic material.

25. The process of claim 24 in which said carbonylation catalyst comprises a carbonyl-forming metal selected from the group Fe, Co, and Ni in the form of a salt, and a halogen selected from the group I, Br, Cl in the form of a free halogen or halogen compound, and the temperature in said acetic acid-synthesis zone is in the range of about 338° to 608° F. and the pressure is in the range of about 15 to 700 atmospheres.

26. The process of claim 24 in which said carbonylation catalyst comprises in admixture (1) a noble metal from the group rhodium, palladium, platinum, iridium, osmium, and ruthenium in the form of an oxide, organometallic compound, salt, or coordination compound; (2) a halogen or halogen-compound promoter; and (3) a dispersant selected from the group, acetic acid and water, pumice, alumina, activated carbon, and silica; and the temperature in said acetic acid-synthesis zone is in the range of 302° to 392° F and the pressure is in the range of about 34 to 680 atm. for liquid-phase reaction.

27. The process of claim 24 in which the temperature in said acetic acid-synthesis zone is in the range of about 392° to 572° F and the pressure is in the range of about 1 to 10 atm. for vapor-phase reaction.

28. The process of claim 24 in which the pressure in said acetic acid-synthesis zone is the same as that in said synthesis-gas generator less ordinary pressure drop in the lines and equipment.

* * * * *

UNITED STATES PATENT AND TRADEMARK OFFICE
CERTIFICATE OF CORRECTION

PATENT NO. : 4,110,359
DATED : August 29, 1978
INVENTOR(S) : CHARLES P. MARION

It is certified that error appears in the above—identified patent and that said Letters Patent is hereby corrected as shown below:

Abstract Line 6 Change "pur" to --pure--

Column 1 Line 61 Change "ad" to --and--

Column 2 Line 59 After "$NH_3$" insert --nil--

Column 3 Line 10 Change "said" to --solid--

Column 3 Line 16 Change "particulte" to --particulate--

Column 14 Line 18 Change "carbonix" to --carbonic--

Column 15 Line 3 Change "leve" to --leave--

Column 17 Line 51 Change "separte" to --separate--

Column 18 Line 2 Change "pruified" to --purified--

Column 20 Line 24 Change "steam" to --stream--

Column 20 Line 68 Change $H_2$ 12 CO + 3 $CO_2$" to --$H_2/2CO+3CO_2$--

*Signed and Sealed this*

*Twenty-ninth* Day of *December 1981*

[SEAL]

Attest:

GERALD J. MOSSINGHOFF

*Attesting Officer*  *Commissioner of Patents and Trademarks*